United States Patent
May

(10) Patent No.: US 7,132,661 B2
(45) Date of Patent: *Nov. 7, 2006

(54) SYSTEM AND METHOD FOR DETECTING WATER VAPOR WITHIN NATURAL GAS

(75) Inventor: Randy Dean May, Glendora, CA (US)

(73) Assignee: SpectraSensors, Inc., San Dimas, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 10/688,723

(22) Filed: Oct. 16, 2003

(65) Prior Publication Data

US 2004/0079887 A1    Apr. 29, 2004

Related U.S. Application Data

(63) Continuation-in-part of application No. 09/941,891, filed on Aug. 28, 2001, now Pat. No. 6,657,198.

(60) Provisional application No. 60/228,494, filed on Aug. 28, 2000.

(51) Int. Cl.
 *G01J 5/02* (2006.01)
 *G01N 21/39* (2006.01)
 *G01N 21/35* (2006.01)

(52) U.S. Cl. .................. 250/343; 250/339.13; 356/436

(58) Field of Classification Search ............ 250/338.5, 250/341.1, 343, 432 R, 435, 339.01, 339.06–339.08, 250/339.1, 339.12–339.13, 353; 73/1.06, 73/29.01–29.02, 335.01, 335.04, 29.05; 356/436–7
See application file for complete search history.

(56) References Cited

U.S. PATENT DOCUMENTS

| | | | |
|---|---|---|---|
| 4,953,390 A | | 9/1990 | Krempl |
| 5,026,991 A | * | 6/1991 | Goldstein et al. ............ 250/343 |
| 5,107,118 A | * | 4/1992 | Murray et al. ............ 250/339.1 |
| 5,528,040 A | * | 6/1996 | Lehmann ..................... 250/343 |
| 5,880,850 A | * | 3/1999 | McAndrew et al. ......... 356/437 |
| 5,963,336 A | * | 10/1999 | McAndrew et al. ......... 356/437 |
| 6,064,488 A | * | 5/2000 | Brand et al. ................. 356/440 |
| 6,188,475 B1 | * | 2/2001 | Inman et al. ................ 356/246 |
| 6,292,756 B1 | * | 9/2001 | Lievois et al. .............. 73/61.44 |

FOREIGN PATENT DOCUMENTS

| DE | 3413914 A | 10/1985 |
|---|---|---|
| DE | 3413914 A1 | 10/1985 |

OTHER PUBLICATIONS

May, Randy D. "Next-Generation Diode Laser Gas Sensors for Environmental and Industrial Monitoring." Proceedings of the SPIE, vol. 3858 (1999), pp. 110-118.*

(Continued)

*Primary Examiner*—David Porta
*Assistant Examiner*—Frederick F. Rosenberger
(74) *Attorney, Agent, or Firm*—Mintz LevinCCohn Ferris Glovsky & Popeo, P.C.

(57) ABSTRACT

A system and method are disclosed for the detection of water vapor in a natural gas background. The system includes a light source operating in a wavelength range such as, 1.877–1.901 μm, 2.711–2.786 μm, or 920–960 nm, passes through the natural gas to be detected by a detector. In one embodiment, the light source is a tunable diode laser and the moisture level is determined by harmonic spectroscopy. In other embodiments, a VCSEL laser is utilized.

21 Claims, 5 Drawing Sheets

OTHER PUBLICATIONS

Reid, J. et al. "Second harmonic detection with tunable diode lasers—Comparison of experiment and theory." Applied Physics B, vol. 26, No. 3 (Nov. 1981), pp. 203-210.*

Silver, J.A. "Frequency-modulation spectroscopy for trace species detection: Theory and comparison among experimental methods." Applied Optics, vol. 31, No. 6 (Feb. 20 1992), pp. 707-717.*

Kessler, William J., et. al., "Near-IR diode-laser-based sensor for ppb-level water vapor in industrial gases", Proc. SPIE-Int.Soc.Opt. Eng.vol. 3537, 1999, pp. 139-149.

Paige, Mark E., "Commercial Gas Sensing with Vertical Cavity Lasers", OSA Trends in Optics and Photonics, Washington, DC, US Jul. 21, 1999, pp. 141-143.

* cited by examiner

SYSTEM AND METHOD FOR DETECTING WATER VAPOR WITHIN NATURAL GAS This patent application is a Continuation-in-Part of U.S. patent application Ser. No. 09/941,891, filed Aug. 28, 2001 now U.S. Pat. No. 6,657,198, which claims the benefit of U.S. patent application Ser. No. 60/228,494, of Dr. Randy D. May, filed Aug. 28, 2000, both of which are hereby fully incorporated by reference.

BACKGROUND OF THE INVENTION

The present invention relates to a system and method for the detection of moisture in natural gas. More specifically, the present invention relates to a technique for determining the level of water vapor present within an industrial natural gas pipeline.

Natural gas has long been used as an energy source because of its low cost and widespread availability. After natural gas is mined, it is purified through several sequential processes, and distributed via networks of underground pipelines that typically transport the gas at a pipe pressure of several hundred pounds per square inch (PSI). Natural gas is sold to the customer as an energy product, and the energy content is generally expressed in British Thermal Units (BTU). The rate that gaseous product is pumped to the customer is measured in standard million cubic feet (SMCF), which is based on the gas volume at a standard pressure and temperature (typically 1 atmosphere pressure/ 14.73 PSI, and 70 degrees F.).

Contaminants in natural gas, such as water, reduce the BTU capacity of the gas, thereby resulting in a less efficient energy product. Contaminants also corrode delivery pipelines over time potentially resulting in serious safety hazards while also necessitating the costly replacement of segments of the pipeline (downtime for the pipelines can cost upwards of several thousand dollars per second). Accordingly, companies engaged in the mining, purification, and distribution of natural gas continuously monitor the quality of the gas at various stages of production and distribution to prevent such occurrences. One contaminant of particular interest is water vapor ($H_2O$). Excessive buildup of water vapor is a primary cause of pipeline corrosion, and it acts to dilute the natural gas thereby reducing its BTU capacity (thereby making the gas a less efficient energy source).

Distributors of natural gas typically have set maximum allowable levels of $H_2O$ within natural gas for various stages of natural gas production and distribution. The final product that is delivered to the customer (usually a large consumer supplier such as Southern California Gas, or Pacific Gas and Electric), is termed "mainline gas." The typical maximum allowable level of $H_2O$ in mainline gas is 7 lbs of $H_2O$ per measured million standard cubic feet of $CH_4$ (MMscf); 1 lb/MMscf is approximately 21.1 parts per million by volume, ppmv). This level is termed the "tariff". When $H_2O$ levels exceed tariff levels, plant operation can be suspended resulting in substantial loss of revenue and associated customer lawsuits.

Conventional techniques for measuring water vapor in natural gas rely primarily on the use of chemical sensors. These sensors operate by monitoring the capacitance or dielectric constant of a sensor element (made from compounds such as phosphorous pentoxide ($P_2O_5$) and aluminum oxide) subjected to a sample from the mainline gas. The electrical properties of the sensors change in a quantitative measurable manner as a function of the amount of water vapor present in the sample gas and such changes are translated into water concentration measurements. In such chemical sensors, a low pressure sample of pipeline gas is delivered to the sensor element via a regulation (pressure reduction) system. The gas sample measured by the pipeline is at a much lower pressure than the pipeline itself (typically 10–30 PSI, compared to 800 PSI in the pipeline). Such sensors are typically housed in sampling shelters that also house the accompanying regulation system.

As the sensing elements in chemical sensors are necessarily exposed to gas samples, contaminants in the gas stream such as glycols, amines, and oils directly contact the sensors. While chemical sensors can provide reliable measurements for short periods of time after calibration, the exposure to the contaminants (glycols and amines in particular) soil the sensor, thereby causing drifts in the calibration. This condition results in erroneous readings and can lead to eventual failure if the contaminants build up. Various filters (coalescing, adsorbents, and particle filters) have been employed to minimize the effects of glycol and amine contamination, but historically these filtration schemes are only temporary solutions. This is due in part because the filters are easily saturated with contaminants or they leak and require replacement at irregular intervals.

It should therefore be appreciated that there remains a need for a reliable and durable system and method for detection of water levels in natural gas.

SUMMARY OF THE INVENTION

The current invention utilizes absorption spectroscopy, a technique that has long been utilized to measure the concentration of water vapor in air, and in various laboratory environments. With such spectroscopy techniques, a light source is passed through a gas sample and detected by a detector opposite the light source. The light source can be a conventional hot filament, a glow bar, a laser, or any suitable emitter in the wavelength region of interest. By monitoring the amount of light absorbed by the sample, at specific wavelengths, the concentration of the target gas can be accurately determined.

A common problem with absorption spectroscopy is interference among constituents in the gas sample being measured. This interference occurs when the gas of interest (in this case $H_2O$) absorbs light at the same, or nearly the same, wavelength as another gas present in the sample. Natural gas, which is composed of greater than 95% $CH_4$, has water vapor at typically less than 1% by volume. Conventional spectroscopic methods (i.e., non-laser based) are not suitable for measurements of $H_2O$ in a $CH_4$ background because the absorption by $CH_4$, which is present in much larger quantities, completely obscures the much weaker absorption by $H_2O$ at all wavelengths in the visible and infrared region.

The current invention operates in a wavelength range with minimal $CH_4$ absorption and preferably utilizes laser light sources for absorption spectroscopy, thereby minimizing the effects of interference due to the extremely high spectral purity of the laser (narrow line width). In some embodiments, the current system incorporates a laser as its light source such as those used in automated, unattended, field instrumentation that operate at wavelengths between 1.6 and 2.7 microns (μm). The preferred lasers are the tunable diode lasers ("TDL") detailed in U.S. Pat. No. 5,257,256, which is hereby fully incorporated by reference. TDLs are widely utilized in optical communications, laser printers, bar code readers, CD players, and laser pointers. Alternatively, a color center laser which operates in the 1–3 μm region may be utilized, but such lasers are not always suitable for use in commercial field instrumentation due to their relatively large physical size, high power consumption, high maintenance requirements (they must be cryogenically cooled), and cost. In addition, other types of light sources may be used such as VCSELs, quantum cascade lasers, color center lasers, that operate at wavelengths that emit light at substantially a single wavelength where water is absorbed at a much greater level than natural gas, such as 920 nm to 960 nm, 1.877–1.901 µm or 2.711–2.786 µm.

Laser-based measurements of water vapor in air use commercially-available TDLs operating at wavelengths near 1.38 µm, where water vapor has a strong absorption band. However, this wavelength is not suitable for measurements of $H_2O$ in a $CH_4$ background because $CH_4$ absorption in the 1.38 micron region is extremely strong and completely obscures absorption by $H_2O$ (see the spectrum of $CH_4$ in the 1–2 µm region 200 which is shown in FIG. 2).

The present system measures water vapor at another absorption band, 1.88 µm, where absorption by $CH_4$ is much weaker (see FIG. 3 which illustrates transmission spectra 300 (transmission=1-absorption) of $CH_4$ 325 and $H_2O$ 350 over wavenumbers 5260–5330 (wavenumber=1 µm, times 10,000)). There are several $H_2O$ absorption lines that can be used to monitor $H_2O$ in a natural gas background, but it is within certain wavelength ranges in the CH4 absorption spectrum, 920 nm to 960 nm, 1.877–1.901 µm or 2.711–2.786 µm, where there are relatively strong $H_2O$ absorption lines, thereby allowing water vapor to be measured in a pure $CH_4$ background (see FIG. 4 which illustrates a spectrum 400 showing the relative positions of the $CH_4$ 425 and $H_2O$ 450 absorption lines over wavenumbers 5322–5336). FIG. 6 illustrates a spectrum 600 showing the relative positions of the $CH_4$ 625 and $H_2O$ 650 absorption lines over wavelengths 2700 nm to 2800 nm—with exemplary absorption lines at 2771.15 nm, 2724.17 nm, 2740.17 nm, 2755.07 nm, 2770.69 nm and 2786.51 nm). FIG. 7 illustrates a spectrum 700 showing the relative positions of the $CH_4$ 625 and $H_2O$ 650 absorption lines over wavelengths 920 nm to 980 nm with several present absorption lines.

To improve detection sensitivity, the current system employs a technique called harmonic spectroscopy in connection with its TDL light source. Harmonic spectroscopy has been used since the 1950s in nuclear magnetic resonance spectrometers, stark spectrometers, and other various laboratory instruments. Harmonic spectroscopy as used in some embodiments of the current system involves the modulation of the TDL laser wavelength at a high frequency (kHz–MHz) and detecting the signal at a multiple of the modulation frequency. If detection is performed at twice the modulation, the term second harmonic spectroscopy is used. Advantages to this technique include the minimization of 1/f noise, and the removal of the sloping baseline that is present on TDL spectra (due to the fact that the laser output power increases as the laser injection current increases, and changing the laser injection current is how the laser is tuned).

Specifically, the present invention is embodied in a system for detecting water vapor in natural gas which includes a light source operating at a wavelength at which water is absorbed at a sufficiently greater level than natural gas, emits light through the natural gas to a detector configured to receive light from the light source, and electronics coupled to the detector for computing the level of water vapor in the natural gas based on the amount of light detected by the detector. In some embodiments, the light source is a tunable diode laser, while in other embodiments, the light source is a color center laser or a quantum cascade laser. Furthermore, the detector is preferably an InGaAs detector. In some embodiments, the emitted light has a frequency in the 1.877–1.901 µm, and in other embodiments, the light is emitted within the range of 920 to 960 nm or 2.711–2.786 µm. Other absorption lines may be utilized where water absorbs light at a sufficiently greater level than natural gas and a light source is available with a sufficiently small line width to emit at or near a single absorption line.

The present invention is also embodied in a method for determining the level of water vapor in natural gas comprising the following steps: providing a light source emitting light at a frequency where water is absorbed at a sufficiently greater level than natural gas, positioning a detector opposite the light source to detect the level of emitted light, supplying a sample of natural gas between the light source and the detector, and determining the concentration of water vapor in the natural gas based on the level of light detected by the detector. In such a method, the gas is preferably taken by a gas line from a main pipeline into a shelter where the light source is housed. In some arrangements, the emitted light has a frequency approximately in the 1.8–1.9 µm, more specifically, 1.877–1.901 µm, and in other variations, the light is emitted approximately at a frequency in the range of 2.7–2.8 µm, and more specifically in approximate range of 2.711–2.786 µm, and in yet other embodiments the light is emitted at a wavelength within the range of 920 nm to 960 nm.

Though the current system is described in connection with the sampling of natural gas from a main pipeline, it will be appreciated that the current system and method could be applied to any situation where it is desirable to measure the moisture content in natural gas or methane such as natural gas purification processes.

DESCRIPTION OF THE PREFERRED EMBODIMENTS

The current system and method relate to the measurement of moisture content in natural gas based on absorption of light at specific wavelengths where water molecules absorbs light strongly. Generally, this technique is referred to as absorption spectroscopy, and is applicable to the measurement of a wide range of gases, liquids, and solids.

Figure 1:
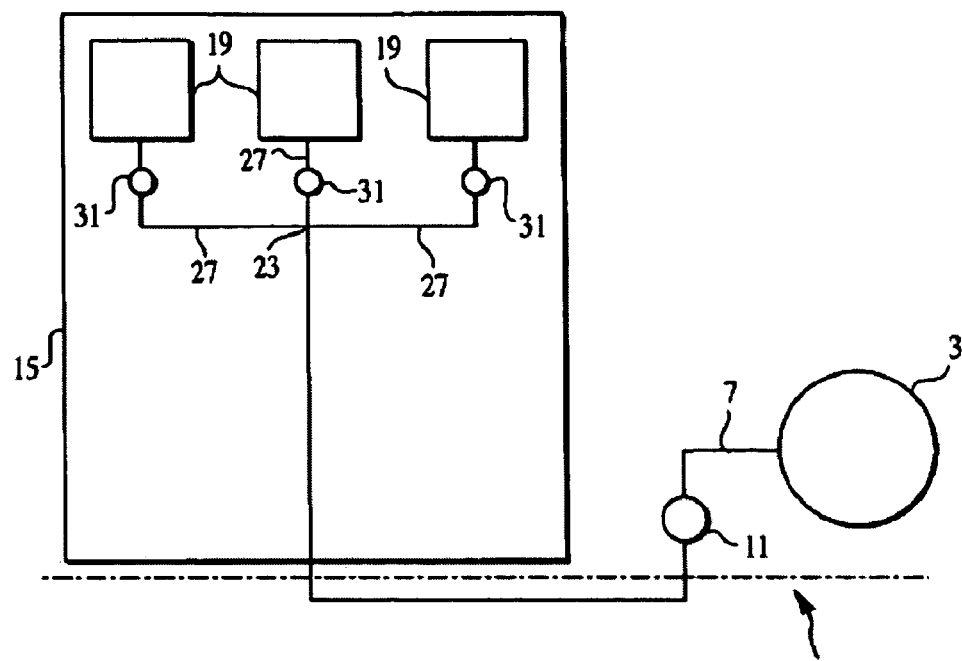
FIG. 1 is a block diagram of a conventional sampling shelter employing chemical sensors for the detection of contaminants in methane.
Figure 2:
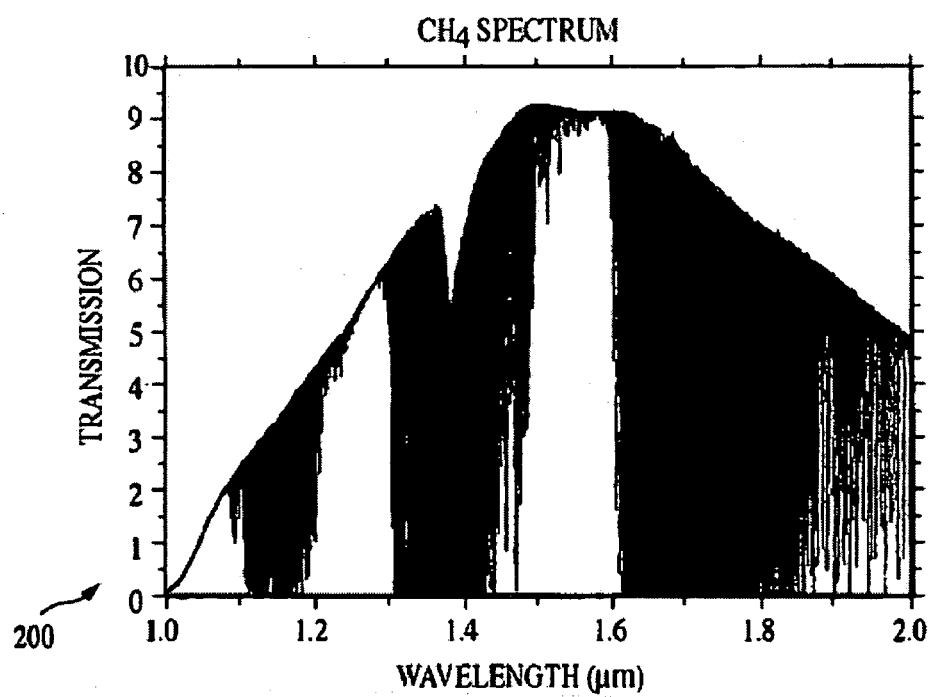
FIG. 2 is a spectrum of methane at wavelengths ranging from 1.0 µm to 2.0 µm.
Figure 3:
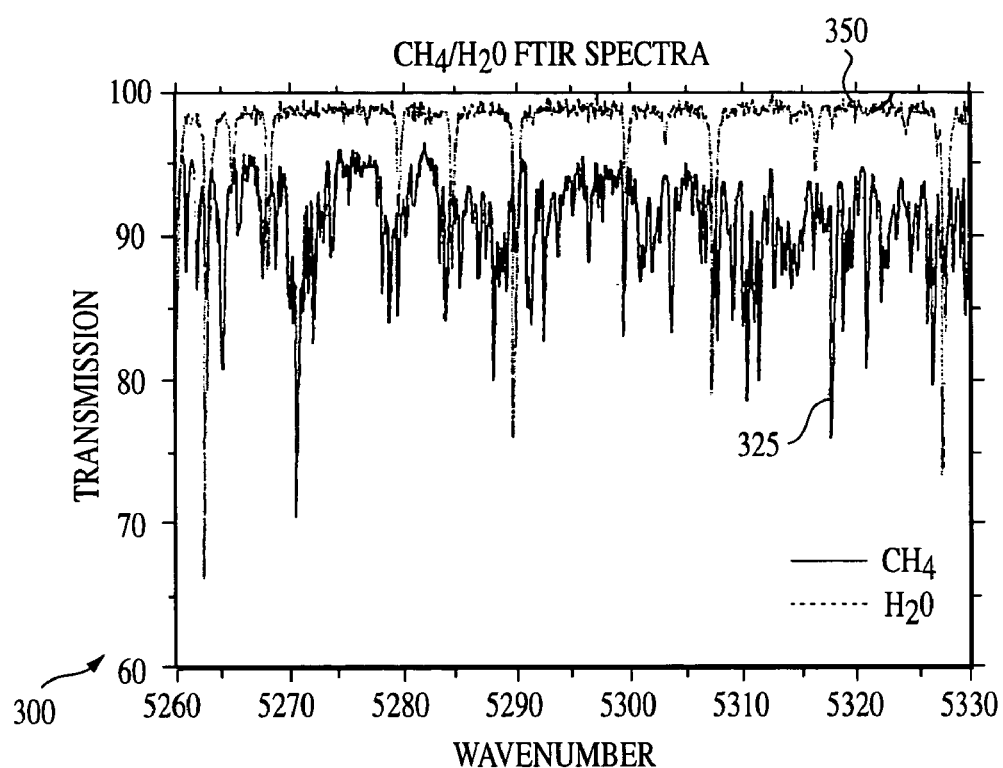
FIG. 3 is a spectrum of methane overlaid with a spectrum of water at wavenumbers ranging from 5260 to 5330.
Figure 4:
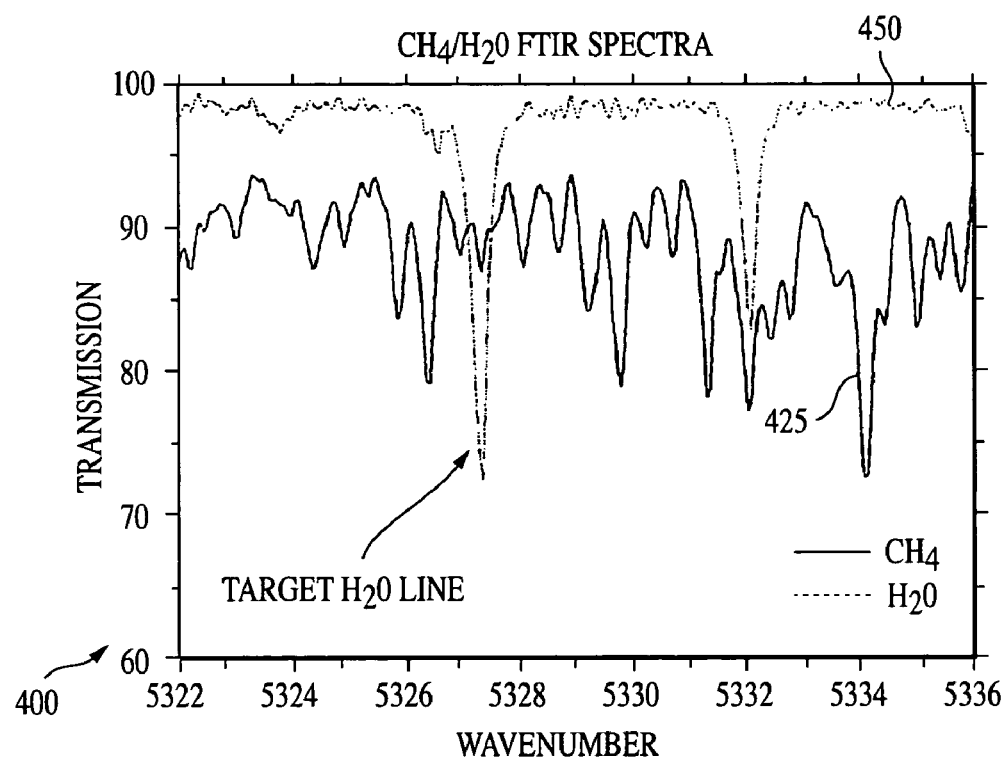
FIG. 4 is a spectrum of methane overlaid with a spectrum of water at wavenumbers ranging from 5322 to 5336.

As seen in FIG. 1, a pipeline 3 of natural gas is coupled to a gas line 7 which includes a regulator 11 for reducing the gas pressure within the gas line. From the regulator, the gas line enters a sampling shelter 15 that houses a plurality of sensors 19 (with at least one being an optical gas sensor as the present invention may be utilized in parallel with the chemical sensors described above). If multiple sensors are employed, they are connected in parallel to the gas line so that gas flow can be simultaneously directed to all of the sensors. This is accomplished after the gas line enters the sampling shelter by diverting gas into a plurality of feed lines 27 at juncture 23. Each of the feed lines are in turn coupled to a sensor and are controlled by a valve 31 to further restrict the flow of natural gas. Preferably, the gas line and the feed lines are made from stainless steel and have outer diameters of 0.25 inches.

Figure 5:
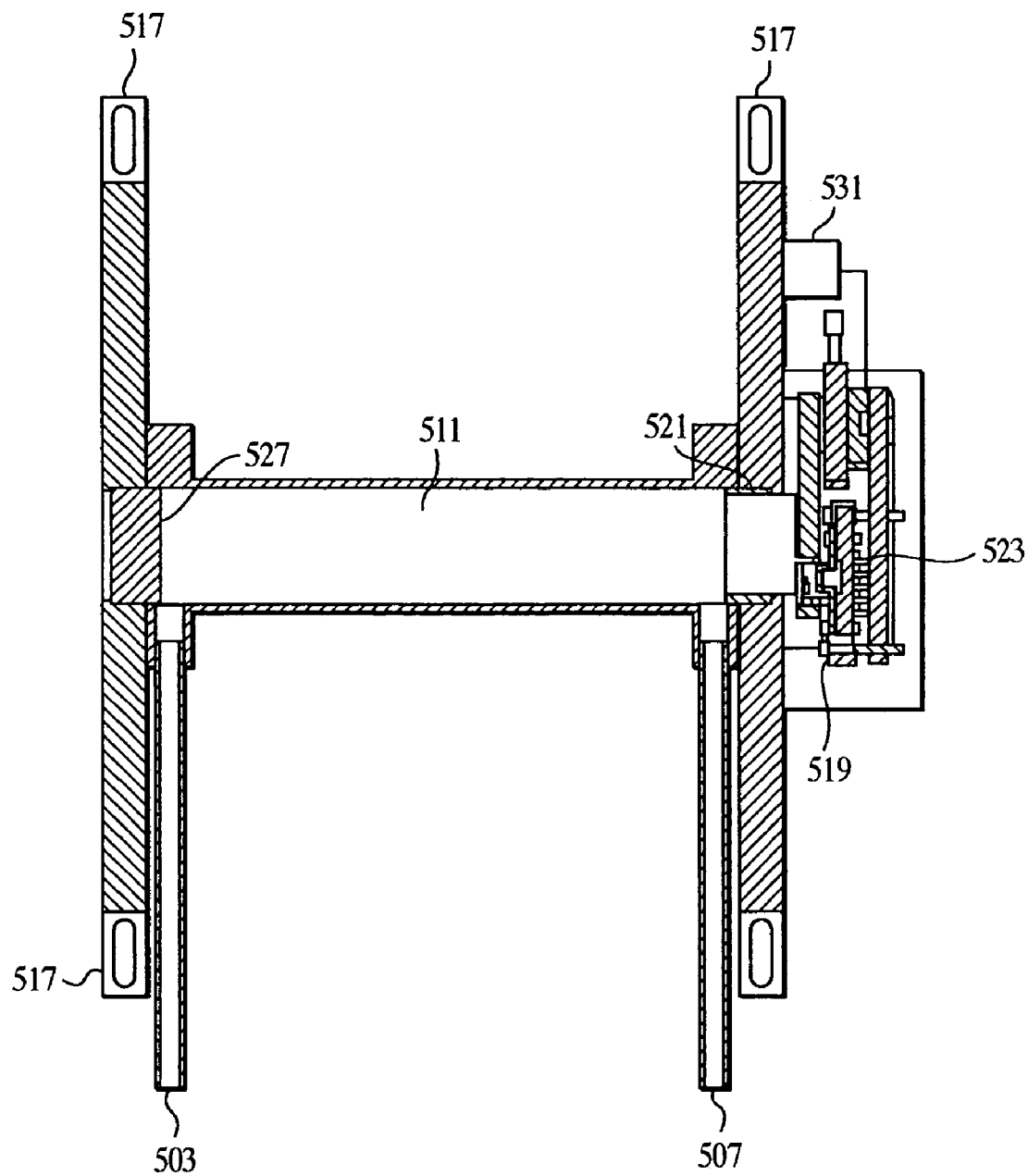
FIG. 5 is a cross-sectional view of the current invention for optically detecting water vapor within natural gas.
Figure 6:
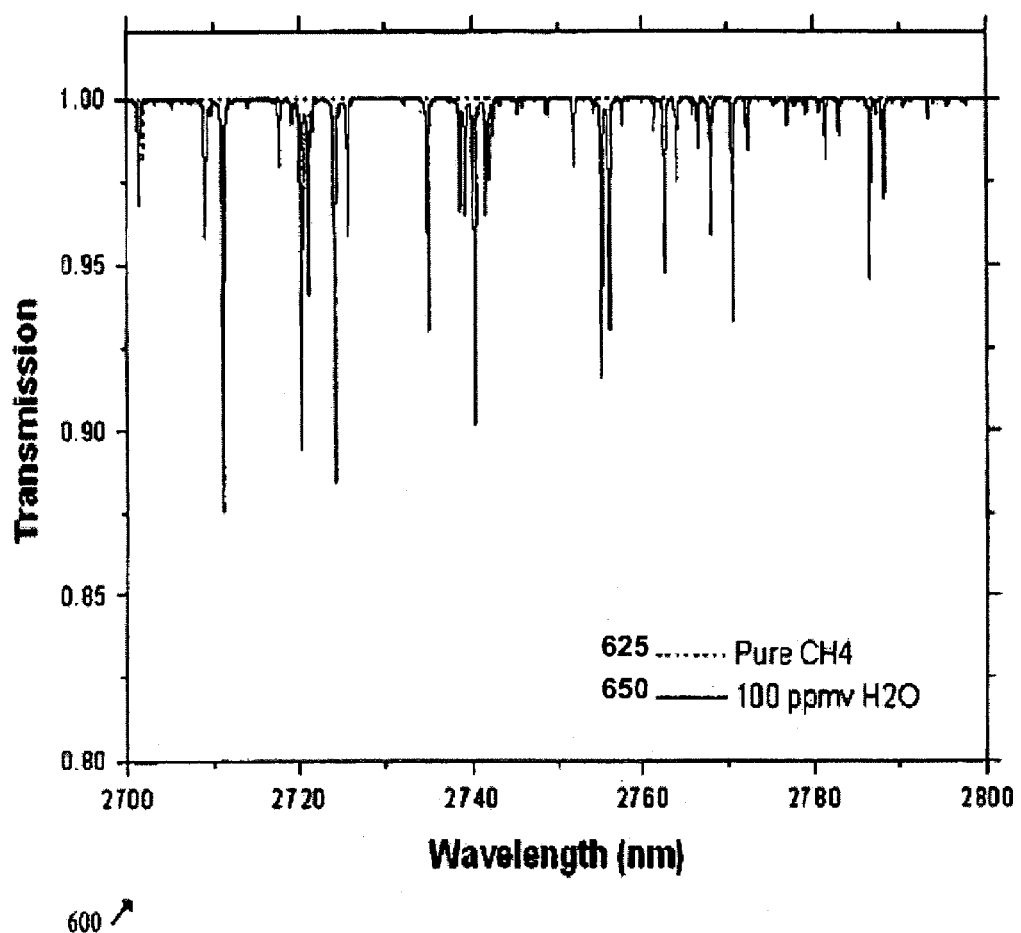
FIG. 6 is a spectrum of methane overlaid with a spectrum of water at wavelengths ranging from 2700 to 2800 nm.
Figure 7:
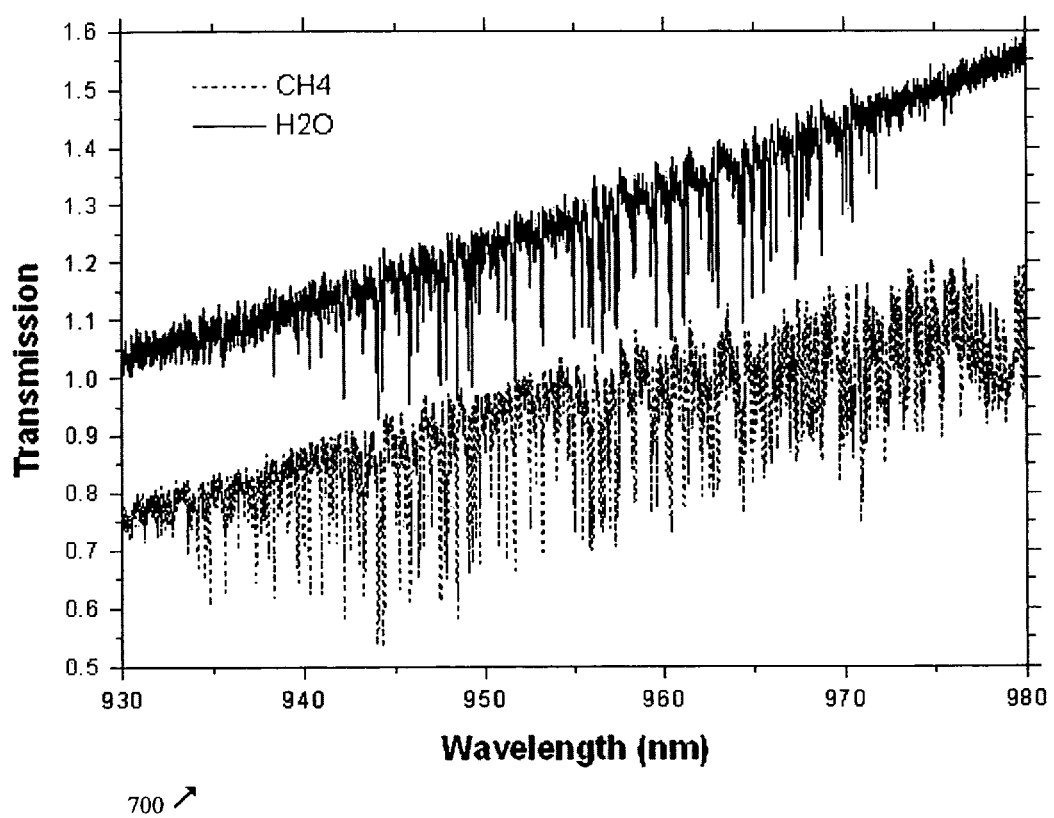
FIG. 7 is a spectrum of methane overlaid with a spectrum of water at wavelengths ranging from 930 to 980 nm.

As seen in FIG. 5, a gas sensor 500 which is incorporated into the sampling shelter 15, includes an inlet 503, an outlet 507, and a light chamber 511, all of which are affixed within an optical gas sensor casing (not shown) through a series of support flanges 517. The casing is configured to house a laser light source 519, an InGaAs detector 523 adjacent to the light source 519, a window coupling the laser light source and the detector to the light chamber, a mirror 527 opposite the laser light source 519, and processing electronics 531. The mirror is positioned preferably in such a manner to reflect light emitted from the light source through the light chamber and the window onto the detector. In one embodiment, the light source is positioned at 5 degrees from horizontal and the mirror is 40 cm from the light source. Preferably, the laser light source is a tunable diode laser or a VCSEL laser configured to emit light either in the 1.877–1.901 $m\mu.m$ wavelength range or within the ranges of 920 nm–960 nm or 2.711–2.786 $m\mu.m$. In one embodiment, the processing electronics includes a 16-bit Motorola microcontroller to convert the signals received by the detector into lbs per measured million cubic feet of methane (1 lb water/mmscf=21 ppm).

In operation, natural gas is fed into the inlet 503 of the gas sensor 500 to continually pass through the light chamber until it exits the gas sensor at the outlet 507. Thereafter, the processing electronics 531 are configured to translate the amount of light absorbed by the natural gas sample into water concentration using known techniques such as those described in article by Randy D. May et al. entitled "Processing and Calibration Unit for Tunable Diode Laser Harmonic Spectrometers", J. Quant. Spectrosc. Radiat. Transfer 49, 335–437, 1993, which is hereby incorporated by reference. Prior to coupling the gas sensor to the main gas line 7, it is preferred that a control sample of natural gas with a known concentration of water is passed through the gas sensor for calibration purposes.

It will be appreciated by one of ordinary skill in the art that standard techniques such as the incorporation of a Herriott cell to replace the single mirror configuration described above may be utilized to increase the effective optical path. For example, the Herriott cell could comprise two opposing Pyrex gold coated mirrors, each preferably with a radius of curvature of 150 mm and a diameter of 25.4 mm. In this embodiment, the tunable diode light source, is configured within the Herriot cell so that the emitted light bounces off each mirror approximately 15 times. This arrangement results in an effective travel path that is 30 times the length between the two mirrors for an effective distance of 4 meters. The light is then detected by the detector, which is coupled to electronics for converting the signals received into water concentration measurements. It should also be recognized that depending on the application, the number of reflections of the Herriott cell may be adjusted. For example, if the water vapor levels will be in the range of 5–100 lb/mmscf, then a single reflection system as described above should be utilized. If the concentration level will be within the range 0–5 lb/mmscf, then a Herriott cell should be utilized.

It will, of course, be understood that modifications to the preferred embodiments will be apparent to those skilled in the art. For example, different techniques may be used for supplying gas samples between the light source and the detector and for converting the signals received by the detector into concentration measurements. Consequently, the scope of the present invention should not be limited by the particular embodiments discussed above, but should be defined only by the claims set forth below and equivalents thereof.

What is claimed is:

1. A system comprising:
    at least one chemical sensor to detect a level of water vapor in natural gas;
    at least one optical sensor to detect a level of water vapor in natural gas, the optical sensor comprising:
        a light source emitting light at substantially a single wavelength having a width sufficiently narrow to conduct single line spectroscopy and corresponding to a single absorption line at which water molecules absorb light at a substantially greater level than natural gas molecules;
        a detector configured to detect the intensity of light emitted from said light source; and
        electronics coupled to said detector for determining the level of water vapor in the natural gas using single line harmonic spectroscopy; and
    a supply line delivering natural gas to the at least one chemical sensor and the at least one optical sensor for parallel measurements.

2. The system of claim 1 wherein said light source is a tunable diode laser.

3. The system of claim 1 wherein said light source is a color center laser.

4. The system of claim 1 wherein said light source is a quantum cascade laser.

5. The system of claim 1 wherein said light source is a VCSEL laser.

6. The system of claim 1 wherein said detector is an InGaAs detector.

7. The system of claim 1 further comprising means for calibrating the optical sensor relative to a known concentration of water vapor within the natural gas.

8. The system of claim 1 wherein the light source operates substantially at a wavelength within the range of 1.877–1.901 μm.

9. The system of claim 1 wherein the light source operates substantially at a wavelength selected from a group comprising: 2.711–2.786 μm.

10. The system of claim 1 wherein the light source operates substantially at a wavelength within the range of 920 to 960 nm.

11. A system comprising:
    Means for chemically detecting a level of water vapor in natural gas;
    Means for optically detecting a level of water vapor in natural gas, the means for optically detecting a level of water vapor in natural gas comprising:
        Means for emitting light at substantially a single wavelength having a width sufficiently narrow to conduct single line spectroscopy and corresponding to a single absorption line at which water molecules absorb light at a substantially greater level than natural gas molecules;

Means for detecting an intensity of light emitted from said means for emitting light; and Calculation means for determining the level of water vapor in the natural gas using single line spectroscopy; and A supply line delivering natural gas to the means for chemically detecting a level of water vapor in natural gas and the means for optically detecting a level of water vapor in natural gas for parallel measurements.

12. The system of claim 11 wherein said means for emitting light comprises a tunable diode laser.

13. The system of claim 11 wherein said means for emitting light comprises a color center laser.

14. The system of claim 11 wherein said means for emitting light comprises a quantum cascade laser.

15. The system of claim 11 wherein said means for emitting light comprises a VCSEL laser.

16. The system of claim 11 wherein said means for detecting comprises an InGaAs detector.

17. The system of claim 11 further comprising means for calibrating the means for optically detecting a level of water vapor in natural gas relative to a known concentration of water vapor within the natural gas.

18. The system of claim 11 wherein said means for emitting light operates substantially at a wavelength within the range of 1.877–1.901 μm.

19. The system of claim 11 wherein said means for emitting light operates substantially at a wavelength selected from a group comprising: 2.711–2.786 μm.

20. The system of claim 11 wherein said means for emitting light operates substantially at a wavelength within the range of 920 to 960 nm.

21. A system comprising:

A chemical sensor to detect a level of water vapor in natural gas; means for optically detecting a level of water vapor in natural gas mounted in parallel to the chemical sensor, the means for optically detecting a level of water vapor in natural gas comprising:

Means for emitting light at substantially a single wavelength having a width sufficiently narrow to conduct single line spectroscopy and corresponding to a single absorption line at which water molecules absorb light at a substantial greater level than natural gas molecules;

Means for detecting an intensity of light emitted from said means for emitting light; and Calculation means for determining the level of water vapor in the natural gas using single line spectroscopy.

* * * * *